United States Patent [19]

Campo et al.

[11] Patent Number: 4,978,802

[45] Date of Patent: Dec. 18, 1990

[54] PROCESS FOR PRODUCTION OF AROMATIC ALDEHYDES

[75] Inventors: Philippe Campo, Montigny-Le-Bretonneux; Panayotis Cocolios, Limours; Paul Dognin, Paris; Henry Ledon, Versailles, all of France

[73] Assignee: L'Air Liquide, Societe Anonyme Pour L'Etude et L'Exploitation des Procedes Georges Claude, Paris, France

[21] Appl. No.: 286,788

[22] Filed: Dec. 20, 1988

[30] Foreign Application Priority Data

Dec. 24, 1987 [FR] France ................. 87 18133

[51] Int. Cl.⁵ ............... C07C 45/29; C07C 45/38
[52] U.S. Cl. .................... 568/432; 568/431; 568/437
[58] Field of Search ............. 568/432, 437, 431

[56] References Cited

U.S. PATENT DOCUMENTS

| | | | |
|---|---|---|---|
| 3,666,815 | 5/1972 | Scheltus | 568/431 |
| 4,429,163 | 1/1984 | Nishizawa et al. | 568/432 |
| 4,471,140 | 9/1984 | Au | 568/432 |

FOREIGN PATENT DOCUMENTS 0012393 12/1979 European Pat. Off. ............ 568/432

OTHER PUBLICATIONS

Kathari et al., J. of Catalysis 41, 180–189 (1976).

Primary Examiner—Werren B. Lone
Attorney, Agent, or Firm—Browdy & Neimark

[57] ABSTRACT

Aromatic aldehydes are produced by oxidation with oxygen of a para-cresol derivative in a solvent, in the presence of a base and a catalytic amount of a cobalt compound. The catalyst is a chelated complex of cobalt with a rigid structure that is slightly oxidizable selected from the group consisting of bis-(4-methylpyridine isoindolinato)cobalt(II) acetate, phthalocyaninatocobalt(II), and sulfophthalocyaninanatocobalt(II). The process is particularly suited to the production of p-hydroxy benzaldehydes.

10 Claims, No Drawings

PROCESS FOR PRODUCTION OF AROMATIC ALDEHYDES

FIELD OF THE INVENTION

This invention relates to a process for the production of aromatic aldehydes, in particular p-hydroxybenzaldehydes.

BACKGROUND OF THE INVENTION

P-hydroxybenzaldehydes are bifunctional molecules which participate a great variety of reactions characteristic of phenol and aldehyde groups. These aromatic aldehydes, particularly p-hydroxybenzaldehyde, are intermediates in the synthesis of various products by way of reactions of catalytic hydrogenation, oxidation, the Canizzaro reaction, reactions with compounds having an active methylene group, heterocyclic syntheses, reactions with amines and amides, formation of cyanophenols or ethers, halogenation, nitration, formation of phenylglycine or salts, and the like.

The most current uses for p-hydroxybenzaldehyde are in agrochemistry, the food industry, pharmacy, polymer and synthetic fiber industries and electroplating.

Industrially, according to the so-called Reimer-Teimann process, described in U.S. Pat. No. 3,365,500, p-hydroxybenzaldehyde is obtained from phenol reacted with chloroform and sodium hydroxide. This process leads to a mixture of ortho/para isomers, with a yield of 60 to 80% relative to the phenol. Although the two products can become independently valuable after separation by distillation, the cost is high. Further, the formation of sodium salts mixed with unreacted phenol requires a recovery treatment of the initial product that is economically unprofitable, and a treatment to make the effluent ecologically acceptable.

According to patent U.S Pat. No. 4,119,671, condensation has been proposed of formaldehyde on formol in a basic medium which leads mainly to a mixture of 2- and 4-hydroxymethylphenols, which are then catalytically oxidized with oxygen into aldehydes. However, this process proves difficult to use because of the great reactivity of the formaldehyde/phenol system which causes the formation of very complex mixtures. Further, the use of this process is limited by the difficulty of separation of two hydroxymethylphenols from the mixture in the presence a base. Yet this operation, which reduces the overall yield of the process, is essential prior to the oxidation stage.

Oxidation of p-hydroxytoluenes to p-hydroxyaryaldehydes by molecular oxygen has also been considered. These oxidation reactions are catalyzed by organic and inorganic salts of cobalt, manganese, chromium or nickel in the presence of sodium hydroxide in methanol. The yields vary from 40 to 80% and depend on both the substrate used and the operating conditions. Following this type of process, European patent application No. 0012939 advocates obtaining derivatives of 4-hydroxybenzaldehyde in the presence of a catalytic amount of a compound of cobalt or metallic cobalt, indicating rather high rates of conversion or selectivity but in an overall manner without isolation of the desired product.

To make obtaining of p-hydroxybenzaldehydes economically interesting and ecologically acceptable a process must be sought that uses a cheap starting product, comprises a minimum number of reaction stages, within the bounds of possibility without intermediate separations, operates under mild conditions, leads to a single isomer with a high conversion, and releases effluents which contain only small amounts of organic material and mineral salts.

SUMMARY OF THE INVENTION

Oxidation of alkylphenols, in particular 4-methylphenol or a substituted derivative, represented by the formula

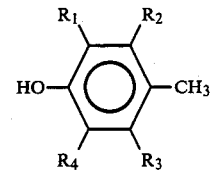

in which $R_1$, $R_2$, $R_3$ and $R_4$ together or separately are hydrogen, a halogen or a lower alkyl radical containing 1 to 4 carbon atoms, in a solvent medium, in the presence of a base, and catalyzed by organic or inorganic salts of transition metals, seems best suited to industrial and specific obtaining of aromatic aldehydes represented by the formula

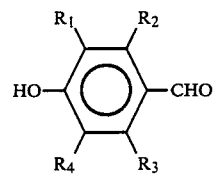

in which $R_1$, $R_2$, $R_3$ and $R_4$ have the same meaning as above, with the proviso, by a judicious choice of the catalyst, of improving both the conversion of the substrate and the selectivity of aldehyde in the form of isolated purified product with the possibility of recycling the catalyst.

The present invention makes it possible to attain this object by performing the oxidation reaction in the presence of a complex of cobalt(II) of the chelated complex type of cobalt with a rigid structure that is slightly oxidizable. This complex is preferably bis-(4-methylpyridine isoindolinato)cobalt(II) acetate (A), phthalocyaninatocobalt(II) (B) or sulfophthalocyaninanato-cobalt(II) (C)

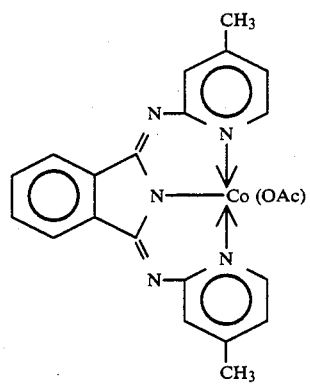

(A)

-continued

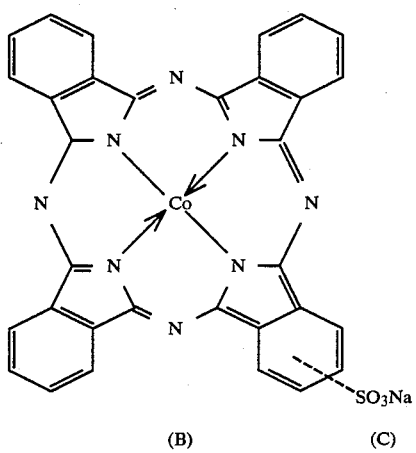

(B)          (C)

The chelated complex is used in a catalytic amount, between 1% and 5% relative to the alkylphenol substrate, in particular between 0.5% and 2%.

The oxidation reaction can be performed in the homogeneous phase in the presence of one or other of the proposed complexes, or in suspension after adsorption of complex (B) or (C) on a support such as activated carbon.

Under identical reaction conditions bis-(4-methylpyridine isoindolinato)cobalt(II) acetate (A), and sulfophthalocyaninatocobalt(II) (C) have performances close to one another. The case is the same with catalyst (B) or (C) deposited on carbon. Further, in the latter case, an easier evolution of the extraction phase and obtaining of a cleaner raw product are observed. Additionally, reuse of the catalyst can be considered, after washing, successively with water and alcohol, then drying, for example, in an oven at around 80° C., without loss of its performances.

Oxidation of 4-methylphenol (p-cresol) with catalyzed oxygen by complex (A), (B) or (C) in a basic methanolic medium leads exclusively to p-hydroxybenzaldehyde. Under mild operating conditions (temperature 60° C., oxygen pressure 0.1 MPa, solvent methanol), conversion of the substrate reaches 100% between 10 and 15 hours, with a selectivity and yield of aldehyde greater than 90%, calculated by the weight of the isolated product.

Oxidation of the alkylphenols is performed in the presence of oxygen, in the form of pure oxygen or oxygen-nitrogen mixtures, in portions adapted to high oxygen content, between 40 and 90% by volume, for example, 80% by volume of oxygen, 20% by volume of nitrogen. It was found that the reaction kinetics is less favorable in the presence of air.

Performance of the oxidation by oxygen under normal pressure (about 0.1 MPa) gives excellent results.

The solvent plays an important role in the evolution of the reaction. Alcohols constitute good solvents and the best results are obtained with methanol. The methanol containing methanol are improved as a function of the reduction of the water content of the methanol. Anhydrous methanol is perfectly suited, and yields are obtained greater than 90% of isolated p-hydroxybenzaldehyde, under a pressure of 0.1 MPa at 60° C., while with methanol-water mixtures the yields are very clearly lower, and in pure water the yield is extremely limited.

In a methanol solvent medium, evolution of the oxidation reaction is observed starting at 20° C., with an improvement of results at 30° C., and an optimization at around 60° C. Performance of the oxidation between 55° C. and 65° C. can advantageously be considered.

The solvent is used in minimal amounts to solubilize the substrate that is to be oxidized, to obtain the maximum concentration of p-cresol at the start, making it possible to obtain a homogeneous liquid medium.

The oxidation can be performed in the presence of different types of bases, such as alkaline hydroxides and alkaline alkoxides; however, the best results are obtained with sodium hydroxide, preferably used in a NaOH/substrate ratio between 1 to 6, particularly between 2.5 and 4.5, in particular about 3.5. There is an optimal base/substrate ratio and an optimal paracresol concentration in the methanol solvent medium to achieve a 100% conversion and a aldehyde selectivity greater than 90%.

The evolution of the oxidation reaction is followed by high-performance liquid chromatography (HPLC) and by consumption of oxygen as a function of time.

After acidification of the reaction mixture, the parahydroxybenzaldehyde is extracted with ethyl acetate, washed with water and dried under reduced pressure and recrystallized in a mixture of dichloromethane/n-hexane in a 1/1 ratio. The product its isolated after recrystallization is identified by comparison of nuclear magnetic resonance ($^1$H NMR) and infrared (IR) spectra with those of a commercial sample of p-hydroxybenzaldehyde, by its melting point (117° C.) and by the melting point of the condensation derivative with p-nitrophenylhydrazine (266° C.).

The process of the invention is applicable to industrial obtaining of aromatic aldehydes, from alkylphenols, in particular 4-methylphenol (p-cresol), 2,4-dimethylphenol, 2,4,6-trimethylphenol, 2,6-ditertiarybutyl-4-methylphenol, and 2-bromo- 4-methylphenol.

The effect of the substituent on oxygen consumption as a function of the oxidation time was studied, particularly for a halogen substituent, bromine, an alkyl monosubstituent, 2-methyl, and alkyl substituents, 2,6-dimethyl and 2,6-ditertiarybutyl. It was observed that alkylphenols carrying electron-donor substituents, such as alkyl substituents, oxidize more rapidly than 4-methylphenol. On the other hand, alkylphenols carrying electron-acceptor substituents such as 2-bromocresol, oxidize more slowly than paracresol.

As above, after stopping of the oxidation reaction, the reaction medium is acidified, aromatic hydroxy aldehyde is isolated, &:he product is washed and purified by recrystallization in solvents suited to the product.

DETAILED DESCRIPTION OF THE INVENTION

Nonlimiting examples of synthesis of aromatic aldehydes are given below.

EXAMPLE 1

Catalytic of oxidation of p-cresol (4-methylphenol) by oxygen

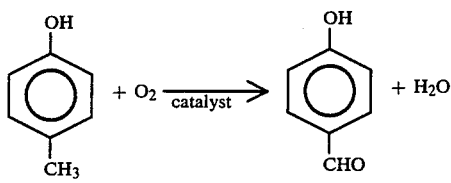

In the various tests, the oxidation was performed under the following conditions: 4-methylphenol: 50 mmol, solvent methanol MeOH; alkaline hydroxide: NaOH; oxygen pressure $PO_2=0.1$ MPa; temperature 60° C.; the catalyst was used in a ratio of 0.5 mol in the form of bis-(4-methylpyridine isoindolinato)cobalt(II) acetate (A) (4- MeBPI) Co(OAc), of sulfophthalocyaninato cobalt(II) PcSCo (C), on carbon (C) PcSCo/Ch, of (C) recycled PcSCo/Ch designated by (R) and phthalocyaninato cobalt(II) (B) on carbon PoSCo/Ch.

The results obtained are given in table I below, in which p- cresol constitutes the substrate designed by: sub. Selectivity: Sel=[aldehyde]/]substrate consumed]×100. The yield: Yld =[aldehyde]/[initial substrate]×100.

[O$_2$]/[aldehyde]=number of moles of oxygen consumed per mole of isolated aldehyde produced (1) Bis (2-methoxyethyl)ether=diglyme
(2): Isolation by precipitation in water
(3): 10% of (p-hydroxybenzyl) methyl ether
(*): Conversion of substrate=[substrate consumed]-/[initial substrate]×100

EXAMPLE 2

SYNTHESIS OF SUBSTITUTED HYDROXYBENZALDEHYDES 2-1. Reaction

In a 250-ml two-neck flask with a water cooler and a partition, there are introduced, under oxygen atmosphere, 175 mmol (7 g) of sodium hydroxide in pellets, 0.5 mmol of cobalt sulfophthalocyanine adsorbed on 3.75 g of activated carbon (120 to 200 mesh), 50 mmol of alkylphenol (25 mmol in case of 3,6-di- tert-butyl-4-methylphenol) and 30 ml of anhydrous methanol (99.95%) The mixture is brought to 60° C. by immersion in an oil bath and kept under stirring. The oxygen is admitted in the reactor by the top of the cooler under 0.105 MPa absolute. A mercury valve set at 0.108 MPa absolute assures tightness of the installation.

The advance of the reaction is followed by:

HPLC analysis of the samples of the reaction mixture taken periodically with a syringe;

recording of the oxygen consumption curve as a function of time, $O_2=f(t)$.

2. Determination and isolation

After stopping the reaction, the catalyst is isolated by filtering under reduced pressure (water-jet pump) and successively washed with methanol, water, then in methanol to entrain the maximum of organic products The volume of filtrate is adjusted to 500 ml by addition of methanol A sample of 5 ml of this solution serves for determination by HPLC of the remaining substrate and aldehyde formed, after addition of suitable standard. The main solution is acidified with 3.3 N hydrochloric acid to pH 4.7.

The isolation phase depends on the product used:

TABLE I

| Test | Conditions | | Aldehyde isolated | Substrate consumed | O$_2$ Consumed | [O$_2$]/[Ald] |
|---|---|---|---|---|---|---|
| 1 | (4-MeBPI)Co(OAc) | mmol | 15.6 | 35.4 | 59.3 | 3.8 |
|  | MEOH 75 ml | Sel | 44.1 | | | |
|  | NaOH/Sub = 2.5 | Yld | 31.1 | 70.8* | | |
| 2 | (4-MeBPI)Co(OAc) | mmol | 14.4 | 40.1 | 57.4 | 3.9 |
|  | MeOH 150 ml | Sel | 35.9 | | | |
|  | NAOH/Sub = 2.5 | Yld | 28.8 | 80.2* | | |
| 3 | (4-MeBPI)Co(OAc) | mmol | 28.7 | 49.1 | 103 | 3.6 |
|  | MeOH 32 ml | Sel | 58.5 | | | |
|  | NaOH/Sub = 2.5 | Yld | 57.4 | 98.2* | | |
| 4 | (4-MeBPI)Co(OAc) | mmol | 7.4 | 31.5 | 44.7 | 6 |
|  | MeOH 32 ml | Sel | 23.6 | | | |
|  | NaOH/Sub = 1.5 | Yld | 14.9 | 63.0* | | |
| 5 | (4-MeBPI)Co(OAc) | mmol | 25.8 | 50 | 103 | 4 |
|  | Piperidine | Sel | 51.7 | | | |
|  | MeOH 32 ml | Yld | 51.7 | 100* | | |
|  | NaOH/Sub = 2.5 | | | | | |
| 6 | (4-MeBPI)Co(OAc) | mmol | 39.9 | 50 | 67 | 1.7 |
|  | MeOH 32 ml | Sel | 79.9 | | | |
|  | NaOH/Sub = 3.5 | Yld | 79.9 | 100* | | |
| 7 | PcSCo | mmol | 41.4 | 50 | 80.7 | 1.9 |
|  | MeOH 32 ml | Sel | 82.7 | | | |
|  | NaOH/Sub = 3.5 | Yld | 82.7 | 100* | | |
| 8 | PsSCo/Charbon | mmol | 42.7 | 50 | 71.1 | 1.7 |
|  | MeOH 32 ml | Sel | 85.5 | | | |
|  | NaOH/Sub = 3.5 | Yld | 85.8 | 100* | | |
| 9 | PcSCo/Ch (R) | mmol | 44.1 | 50 | 66.6 | 1.5 |
|  | MeOH 32 ml | Sel | 88.2 | | | |
|  | NaOH/Sub = 3.5 | Yld | 88.2 | 100* | | |
| 10 | PcSco/Ch | mmol | (3)46 | 50 | 72.2 | 1.6 |
|  | MeOH 32 ml | Sel | 92 | | | |
|  | NaOH/Sub = 3.5 | Yld | 92 | 100* | | |
|  | Diglyme(1)0.6 ml | | | | | |
| 11 | PcCo/Ch (2) | mmol | 31.5 | 34 | 91 | 2.9 |
|  | MeOH 32 ml | Sel | 93.5 | | | |
|  | NaOH/Sub = 3.5 | Yld | 63 | 67* | | |

(a) 3,5-di-tert-butyl-4-hydroxybenzaldehyde:

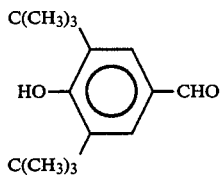

After acidification, a formation of a precipitate is observed which is filtered under reduced pressure, washed with water, then dried on $P_2O_5$ (19 Pa) Melting point: 185° C., w=2.45 g (10.5 mmol), Yield=42%.

(b) 4-hydroxy-3-methylbenzaldehyde:

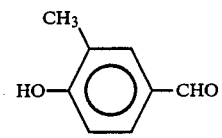

After acidification, the filtrate is evaporated dry. The solid residue is taken up with acetonitrile. The mineral salts present are insoluble and eliminated by filtration. The filtrate, after evaporation, leads to an oil containing 70% aldehyde and 30% of the starting product ($^1$H NMR and HPLC checking). The aldehyde is isolated by successive treatments of the oil with mixtures $CH_2Cl_2$/n-$C_6H_{14}$ 1/10 and $Et_2O$/n-$C_6H_{14}$ 1/10 and dried on $P_2O_5$ (19 pascals). (19 pascals). Melting point=109° C., w=2.40 g (17.6 mmol), Yld=35%.

(c) 4-hydroxy-3,5-dimethylbenzaldehyde:

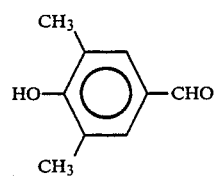

After acidification and reduction of the volume of the solvents by evaporation under reduced pressure, a precipitate is obtained. After filtration and washing with water, it is dried on $P_2O_5$ (19 Pa). Melting point=116° C., w=4.1 g (27.3 mmol), Yld=59%.

(d) 3-bromo-4-hydroxybenzaldehyde:

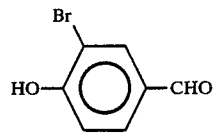

The aldehyde isolated as in the preceding case contains 10% of the starting product ($^1$H NMR checking) which is easily eliminated by washing of the solid residue with hexane.

Melting point=132° C., w=5.28 g (26.3 mmol), Yld=53%.

2-3-HPLC analysis
WATERS NOVAPACK C18 column
UV detection: 270 nm
eluant: A/B/C/=MeOH/MeCN/$H_2O$ pH=4 ($H_2SO_4$)

| ALDEHYDE | ELUANT A/B/C | OUTPUT ml/min | STANDARD |
|---|---|---|---|
| DITERTBUTYL | 40/40/20 | 0.5 | 3-methyl-benzonitrile |
| METHYL | 20/20/60 | 1.0 | benzonitrile |
| DIMETHYL | 20/20/60 | 0.5 | 4-hydroxy-benzonitrile |
| BROMO | 20/20/60 | 1.0 | 4-hydroxy-benzonitrile |

The results obtained are given in table II below.

TABLE II

| Test | Substituent Substrate | | Aldehyde CLHP | Aldehyde isolated | Substrate consumed | $O_2$ Consumed | $[O_2]/[Ald]$ CLHP |
|---|---|---|---|---|---|---|---|
| 1 | ditert-butyl-2,6 | mmol | 11.7 | 10.5 | 25* | 65 | 5.6 |
| | | sel | 47 | 42 | | | |
| | | Rdt | 47 | 42 | (100) | | |
| 2 | methyl-2 | mmol | 21.9 | 17.6 | 45 | 74 | 3.4 |
| | | Sel | 49 | 39 | | | |
| | | Rdt | 44 | 35 | (89) | | |
| 3 | dimethyl-2,6 | mmol | 33 | 27.3 | 50 | 103 | 3.1 |
| | | Sel | 66 | 55 | | | |
| | | Rdt | 66 | 55 | (100) | | |
| 4 | bromo-2 | mmol | 32.9 | 27.4 | 34 | 50 | 1.5 |
| | | Sel | 97 | 81 | | | |
| | | Rdt | 68 | 55 | (70) | | |

( ) conversion of substrate
*Substrate used = 25 mmol
Temperature: 50° C.
Substrate: 50 mmol
Sodium hydroxide: 175 mmol
Catalyst: 0.5 mmol
Solvent: methanol 30 ml.

The foregoing description of the specific embodiments will so fully reveal the general nature of the invention that others can, by applying current knowledge, readily modify and/or adapt for various applications such specific embodiments without departing from the generic concept, and therefore such adaptations and modifications are intended to be comprehended within the meaning and range of equivalents of the disclosed embodiments. It is to be understood that the phraseology or terminology herein is for the purpose of description and not of limitation.

What is claimed is:

1. A process for the production of aromatic aldehydes having the formula

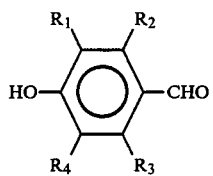

in which each of $R_1$, $R_2$, $R_3$ and $R_4$ selected from the group consisting of hydrogen, a lower alkyl radical and halogen, by reacting an alkylphenol of the formula

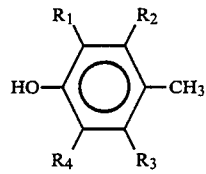

In which $R_1$, $R_2$, $R_3$ and $R_4$ have the same meaning as above, with oxygen, in a solvent medium in the presence of a base and a catalytic amount of a cobalt compound, wherein the oxidation reaction of the substrate is performed in the presence of a catalyst consisting of a chelated complex of cobalt(II) selected from the group consisting of bis-(4-methylpyridine isoindolinato)cobalt (II) acetate, phthalocyaninatocobalt(II) and sulfophthalocyaninanatocobalt(II).

2. A process for the production of aromatic aldehydes according to claim 1, wherein the phthalocyaninatocobalt(II) and sulfophthalocyaninanatocobalt (II) are adsorbed on a support.

3. A process for the production of aromatic aldehydes according to claim 1, wherein the oxidation reaction is performed in the presence of from 1% and 5% of catalyst relative to the alkylphenol.

4. A process for the production of aromatic aldehydes according to claim 1, wherein the oxidizing gas is selected from the group consisting of pure oxygen and oxygen-nitrogen mixtures with an oxygen content of between 40 and 90% by volume.

5. A process for the production of aromatic aldehydes according to claim 1, wherein the oxidation is performed under normal pressure of about 0.1 MPa.

6. A process for the production of aromatic aldehydes according to claim 1, wherein the solvent medium is anhydrous methanol used in the minimum amount required for dissolving the substrate.

7. A process for the production of aromatic aldehydes according to claim 1, wherein the oxidation reaction is performed at a temperature between 55° and 65° C.

8. A process for the production of aromatic aldehydes according to claim 1, wherein the base is sodium hydroxide and said base is used in a NaOH/substrate ratio of between 1 and 6.

9. A process for the production of aromatic aldehydes according to claim 1, wherein the alkylphenol is selected from the group consisting of 4-methylphenol, 2,4-dimethylphenol, 2,4,6-trimethylphenol, 2,6- ditertiarybutyl-4-methylphenol, and 2-bromo-4-methylphenol.

10. A process for the production of aromatic aldehydes of the formula

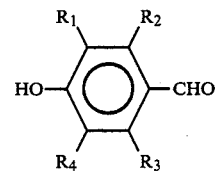

in which each $R_1$, $R_2$, $R_3$ and $R_4$ is selected from the group consisting of hydrogen, lower alkyl, and halogen, by the reaction of an alkylphenol of the formula

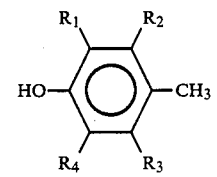

in which $R_1$, $R_2$, $R_3$ and $R_4$ have the same meaning as above, with oxygen, in a solvent medium in the presence of a base and a catalytic amount of a cobalt compound, wherein the oxidation reaction of the substrate is performed under the following conditions:
(a) in the presence of a catalyst consisting of a chelated complex of cobalt (II) selected from the group consisting of bis-4(4-methylpyrridine isindolinato) cobalt (II) acetate, phthalocyaninatocobalt (II) and sulfophthalocyaninanatocobalt (II);
(b) the catalyst is used in an amount between 1% and 5% relative to the substrate;
(c) the oxidizing gas consists of pure oxygen or oxygen-nitrogen mixtures with an oxygen content of between 40% and 90%.
(d) the oxidation is performed under normal pressure and a temperature between 55° and 65° C.;
(e) the base consisting of sodium hydroxide is used in a NaOH/substrate ration between 1 and 6.

* * * * *